United States Patent [19]

Chen et al.

[11] Patent Number: 5,564,422

[45] Date of Patent: Oct. 15, 1996

[54] METHOD AND APPARATUS FOR IMPROVED PREDICTION OF TRANSVENOUS DEFIBRILLATION THRESHOLD

[76] Inventors: Peng-Sheng Chen, 4925 Oakwood Ave., La Canada, Calif. 91011; Charles D. Swerdlow, 15722 Castlewoods Dr., Sherman Oaks, Calif. 91403

[21] Appl. No.: 415,369

[22] Filed: Apr. 3, 1995

[51] Int. Cl.$^6$ ..................................................... A61N 1/39
[52] U.S. Cl. ................................................ 128/697; 607/8
[58] Field of Search ................................. 607/8, 7, 4, 5; 128/696, 697

[56] References Cited

U.S. PATENT DOCUMENTS 5,105,809  4/1992  Bach, Jr. et al. .
5,346,506  9/1994  Mower et al. .

OTHER PUBLICATIONS

"Relation Between Upper Limit of Vulnerability and Defibrillation Threshold in Humans", Chen et.al., Circulation vol. 88, No. 1, 186–92(Jul. 1993).

*Primary Examiner*—William E. Kamm
*Assistant Examiner*—Kennedy J. Schaetzle
*Attorney, Agent, or Firm*—Brad Pederson

[57] ABSTRACT

A system and method for predicting the defibrillation threshold energy of a defibrillation lead arrangement by determining the upper limit of vulnerability of the heart by shocking the heart at varying times during the T-wave at decreasing test shock energy levels until fibrillation is induced in the heart. The lowest energy level which fails to induce fibrillation is determined to be the upper limit of vulnerability and the defibrillation threshold is predicted to be an energy level incrementally higher in the range of about 5 Joules.

14 Claims, 2 Drawing Sheets

METHOD AND APPARATUS FOR IMPROVED PREDICTION OF TRANSVENOUS DEFIBRILLATION THRESHOLD

FIELD OF THE INVENTION

The present invention is related to implantable cardiac defibrillators, and in particular to an improved method and apparatus for determining the minimum electrical energy to reach the defibrillation threshold.

BACKGROUND OF THE PRESENT INVENTION

Heart disease remains the number one cause of death in the United States. It is estimated that as many people die from heart disease as from all other causes combined. For many cardiac patients, the cause of death is ventricular arrhythmia in the form of a sudden ventricular tachycardia or ventricular fibrillation that often occurs with little warning.

Ventricular tachycardia is a fairly regular cardiac rhythm disturbance originating in the ventricles which results in a ventricular rate that is too fast to effectively pump blood. Ventricular fibrillation is a chaotic rhythm that is incapable of pumping any blood. In both circumstances, if the blood flow is not reestablished within about three minutes the victim will begin to suffer irreversible brain damage and will most likely succumb within six minutes from the onset of the ventricular arrhythmia.

A substantial number of patients who suffer a bout of ventricular tachycardia or fibrillation survive, only to eventually succumb at a later time to a recurrence of their rhythm disturbance. It is for the benefit of these patients that implantable cardiac defibrillators (ICD) are being developed and refined.

In general, these devices accomplish defibrillation of the heart by delivering an electrical countershock to the myocardium via implanted electrode leads of sufficient strength to terminate the abnormal rhythm. In effect, the ICD simultaneously depolarizes the heart breaking the abnormal rhythm cycle thereby providing an opportunity for the patient's underlying normal rhythm to reestablish. The units are implanted within the patient and connected to the heart through various electrodes to provide continuous monitoring and immediate countershocking when a rhythm disturbance is detected. Because the devices must be small enough for convenient implantation, ICD's are limited in their ability to store electrical energy.

It is important to reliably deliver a sufficiently strong electrical shock to insure defibrillation in response to each occurrence of fibrillation. One method might be to use a set amount of energy known to defibrillate each time. However, this approach is an inefficient use of the limited stored electrical energy and will unnecessarily limit the useful life of a device equipped with this method. It is well known in the art that the energy required to effectively defibrillate a human heart varies with the implanted lead configuration and placement as well as the individual heart's responsiveness to the electrical countershock. To maximize efficiency and still retain integrity to effect defibrillation, it is necessary to determine as accurately as possible the minimal energy level necessary to defibrillate the patient's heart, i.e., the defibrillation threshold (DFT) after the device and the leads are implanted.

One known method of determining the DFT energy of an implantable system is to induce fibrillation with an electrical shock. The heart is then defibrillated through the implanted defibrillation leads. Initially, defibrillation is attempted at a relatively high energy level. If successful in defibrillating the heart, fibrillation is reinitiated and the defibrillation is attempted at a lower energy level. This process is repeated with successively lower defibrillation countershocks until the shock does defibrillate the heart. In this way, a DFT is established and the defibrillation energy level for the ICD is then set at an estimate of the lowest level that can reliably achieve defibrillation given the safety margin above. The significant disadvantage to this method is the necessity to repeatedly fibrillate and then defibrillate the patient's heart to determine the DFT.

Another method of determining defibrillation thresholds is disclosed in U.S. Pat. No. 5,105,809, issued Apr. 21, 1992. The method disclosed begins by applying an initial electrical shock to the patient's heart during a period of vulnerability. The period of vulnerability usually occurs contemporaneously with the T-wave of a standard electrocardiogram (ECG). The energy level of the initial shock is sufficiently high so as not to cause fibrillation. Assuming this initial shock fails to induce fibrillation, a second shock of less magnitude is delivered during a subsequent vulnerability period. The process is repeated with successive shocks of lesser magnitudes until fibrillation is induced. When fibrillation finally occurs, the energy of the preceding shock that did not cause fibrillation is deemed to be the energy level required to defibrillate for that particular lead configuration.

Unfortunately, the vulnerability period on which this technique relies differs from patient to patient and is not necessarily contemporaneous with the T-wave. As a result, this method is susceptible to inefficiency because the time period during the T-wave at which the testing is undertaken may have a substantially different vulnerability than at other points during the T-wave. This method substantially misses the most vulnerable period during the T-wave. This discrepancy will not be appreciated at the time of implantation and therefore substantially underestimates the defibrillation threshold setting.

Another method for establishing a defibrillation threshold is disclosed in U.S. Pat. No. 5,346,506, issued Sep. 13, 1994. The method disclosed relies on research demonstrating that the 50% probability of successful defibrillation can be closely approximated by determining the 50% probability of reaching the upper limit of vulnerability (ULV). See "Relation Between Upper Limit of Vulnerability and Defibrillation Threshold in Humans", Chen eta., Circulation vol. 88, no. 1, 186–92 (July 1993). The electrical energy is applied to the heart through epicardial patches at a predetermined limited period of time centered on the mid-upslope of the T-wave. The disclosure argues that by not having to scan the entire T-wave with shocks the total number of shocks is reduced. The disadvantage to this disclosure is that the energy level for the first application is estimated beforehand. The number of shocks required to determine the DFT is reduced only if the estimated 50% probability of reaching the upper limit of vulnerability is quite accurate.

Each of these methods necessitate the use of multiple electrical energy shocks to be delivered from an implantable device of limited storage capacity. Each test shock depletes energy from the device thereby decreasing the expected useful life-span of the device. Additionally, these repeated shocks and episodes of fibrillation take a significant toll on the patient. Considerable time must be spent between test cycles in order to provide the patient's heart time to recover from the previous round of shocks. Because the patient is typically under general anesthesia, then delays in determining the appropriate DFT increase the patient's anesthesia risk. Accordingly, it would be desirable to provide an ICD that is convenient to implant and reliable to use, and that can be used to quickly determine the defibrillation threshold using the least number of test shocks possible and minimizing the patient's risk to only one episode of fibrillation.

SUMMARY OF THE INVENTION

The present invention provides a system and method of determining the defibrillation threshold for an individual patient by determining the heart's upper limit of vulnerability using at least one intravenous defibrillation electrode within the system.

The present invention relates to a system and method for determining the minimal defibrillation energy required to defibrillate a patient's heart by determining the ULV during the vulnerable period corresponding to the T-wave of the ECG. The heart is paced so that precise timing of the peak of the T-wave can be made. Test shocks are then delivered to the heart at 0, 20 or 40 msec prior to the peak of the T-wave beginning with a shock strength predicted to be above the ULV. Each test shock is delivered one minute apart. If the first test shock at the peak of the T-wave fails to induce ventricular fibrillation, the next shock will be delivered at the same strength but with a different interval. If ventricular fibrillation is not induced after three attempts corresponding to the three time intervals, the shock strength is decreased by 5 J and three shocks are delivered again at 0, 20 and 40 msec prior to the peak of the T-wave. The procedure is repeated until ventricular fibrillation is induced. The last shock strength that does not induce fibrillation is the ULV which has been demonstrated to be an accurate estimate of the DFT. If no ventricular fibrillation is induced with 5 J shocks, the ULV and therefore the DFT is predicted to be less than or equal to 5 J.

The ULV is the electrical shock strength at or above which ventricular fibrillation is not induced when an electrical stimulus is delivered during the vulnerable phase of the cardiac cycle. The ULV hypothesis of defibrillation states that a shock may fail to defibrillate, even though it terminates all reentrant wavefronts, because it is delivered during the vulnerable period of some myocardium and thereby reinitiates fibrillation. This hypothesis implies a relationship between the ULV during fibrillation and the DFT. It further implies that measurement of the ULV during paced rhythm can predict the DFT if the relationship between the ULV during fibrillation and the ULV during paced rhythm is known.

The present invention requires delivery of only three shocks in regular rhythm at each shock strength and induction of a maximum of one episode of ventricular fibrillation. The present invention thereby substantially reduces the risks associated with repeated inductions ventricular fibrillation and the risks of many shocks in regular rhythm. The present invention also shortens the time required for the procedure by diminishing the number episodes of ventricular fibrillation, the number of shocks in regular rhythm and the waiting periods between the ventricular fibrillation episodes. Finally, the present invention is simple to apply because the peak of the T-wave is easily identified in all patients.

It is a primary object of the present invention to provide an automatic ICD that can quickly and accurately determine the DFT of the patient by evaluating the heart's ULV after implantation.. This ULV has been shown to be closely correlated to the DFT under appropriate conditions of testing. Recent progress in the development of ICD's has provided for the use of intravenous defibrillation electrodes to complement intravenous pacer and sensor electrodes. Research in the evaluation of the ULV now suggests that the determination of the ULV as disclosed in U.S. Pat. No. 5,346,506 using epicardial patch electrodes is not a valid method for intravenous electrodes. Accordingly, the present invention solves this problem.

It is another object of the present invention to reduce the number of test shocks and episodes of fibrillation experienced by the patient during the testing substantially reducing the risk to the patient.

It is yet another object of the present invention to reduce the number of test shocks and episodes of fibrillation reducing the amount of energy expended in determining the minimum defibrillation energy of an ICD needed to reliably and repeatedly defibrillate an ailing human heart.

The above and other objects and advantages will become more readily apparent when reference is made to the following description, taken in conjunction with the accompanying drawings, and are in no way intended to limit the scope of the present invention.

DETAILED DESCRIPTION

Figure 1:
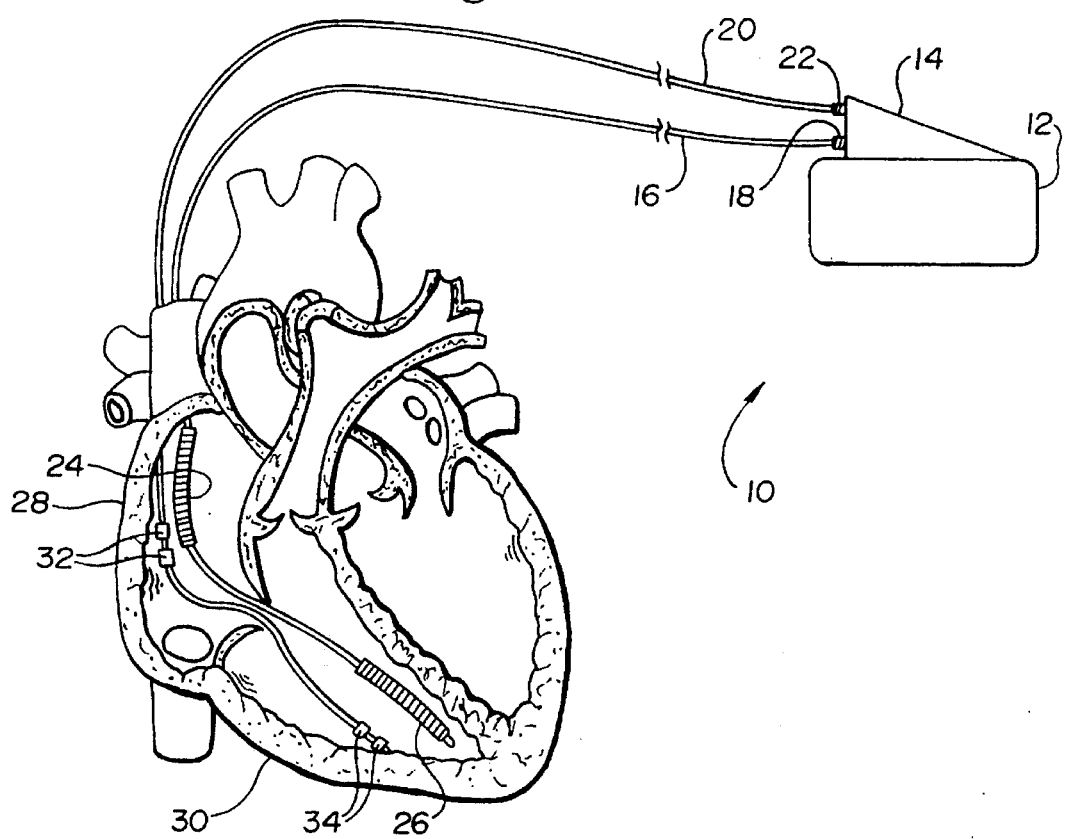
FIG. 1 is an anterior sectional view of a human heart in relative anatomical position, depicting the relative positioning of intravascular electrode catheters and an ICD according to the present invention.

Referring first to FIG. 1, an embodiment of the present invention is depicted as an implantable cardioverter defibrillator system 10 comprising an implantable electrical pulse generating housing 12, an electrical connector pin housing 14, an implantable intravascular discharge catheter 16 electrically connected to pin housing 14 via a pin connector 18, and an implantable intravascular pacing/sensing catheter 20 electrically connected to pin housing 14 via a pin connector 22. Discharge catheter 16 carries proximal defibrillation discharge electrode 24 and distal defibrillation discharge electrode 26 and is configured to position proximal electrode 24 within right atrium 28 and position distal electrode 26 within right ventricle 30. Pacing/sensing catheter 20, as depicted, carries two sets of pacing/sensing electrodes, a proximal electrode set 32 positioned within the right atrium 28 and a distal electrode set 34 positioned within the right ventricle 30. The catheters, discharge electrodes and pacing/sensing electrodes may be of any design known to the art and are not necessarily constrained to just the configuration or combination depicted. The positioning of the defibrillation electrodes is critical such that at least one electrode must be intravascular, with a preferred embodiment using a defibrillation electrode at the right ventricular apex. Positioning of the sensing electrode is not critical so long as an accurate indication of the electrical activity of the heart can be ascertained. Positioning of pacing electrodes is likewise not critical so long as pacer capture is reliable.

Because defibrillation thresholds vary with electrode placement and lead configuration, as well as with the responsiveness of a particular patient's heart, the ULV is best determined after the electrodes and leads have been implanted. In this manner, the threshold corresponds to the particular arrangement used.

Figure 2:
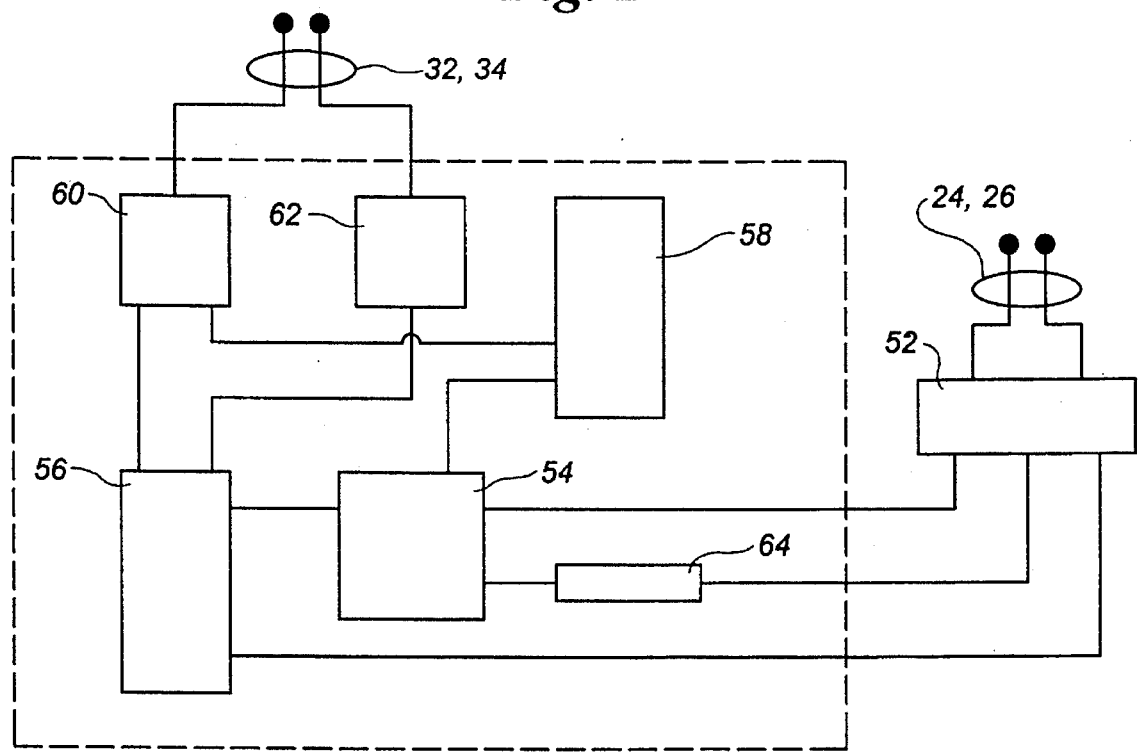
FIG. 2 is a schematic block diagram depicting a suitable arrangement for an ICD according the present invention.

Referring now to FIG. 2, an upper limit of vulnerability (ULV) subsystem 50 according to the present invention is depicted in one possible configuration in electrical connection with a defibrillation subsystem 52. Subsystem 50 and defibrillation subsystem 52 are component subsystems of ICD 10 of FIG. 1 and are contained within housing 12 and electrically connected. ULV subsystem 50 includes a ULV test driver 54, a test/treatment selector 56, a timing circuit 58, a sensing circuit 60, a pacing circuit 62, and a memory unit 64. Defibrillation subsystem 52 may be of any design known to the art, but preferably is programmable to deliver either monophasic or biphasic countershocks, having variable tilt, and controllable through a step wise range of energy outputs from at least 5 J to at least 30 J.

Figure 4:
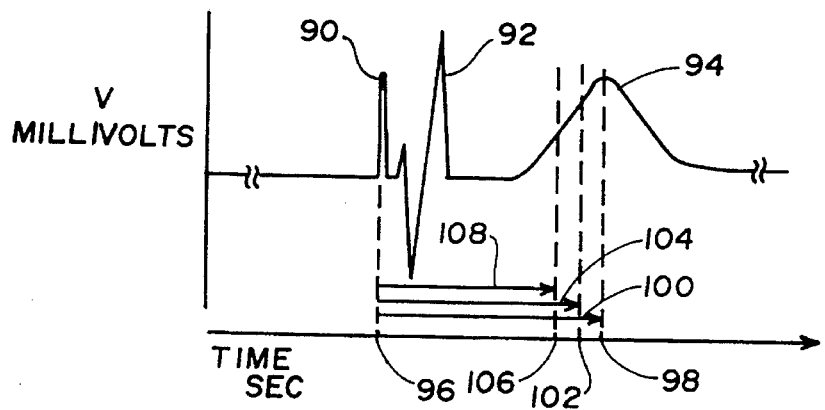
FIG. 4 is a timing diagram depicting the relationship between a paced cardiac cycle and test electrical shocks in accordance with the present invention.

The operation of system 10 will be described in reference to FIGS. 1, 2, and 4. Selector 56 is set to test providing a starting energy level value and triggering sensing circuit 60 to detect the heart's intrinsic rate and provide this value to selector 56. The starting energy level value is stored in memory unit 64. The intrinsic heart rate value is passed to pacing circuit 62. Pacing circuit 62 then provides a baseline pacing output through to electrodes 32, 34 that is of a rate sufficient to overdrive the heart's intrinsic rate. The sensing circuit then evaluates the ECG for the presence of a pacer spike 90, a QRS 92, and a T-wave 94, as shown in FIG. 4. The present invention anticipates an ability to evaluate the ECG signals derived from a number of different lead configurations including skin surface leads as well as intracardiac leads. Examples of sensing lead combinations may include leads in the right atrium, the right ventricle and combinations of electrodes such as between a lead tip electrode and a defibrillation electrode or combinations including pairing leads from the right atrium to the right ventricle or a set of surface electrodes. The present invention evaluates the T-wave morphologies from the combinations of electrodes provided and selects, for timing purposes, that lead combination which provides a monophasic T-wave having the latest occurring peak. Timing circuit 58 now determines a time interval 100 in milliseconds measured from pacer spike 90 to the peak 98 of T-wave 94. The starting energy value and time interval 100 are passed to ULV test driver 54 which triggers defibrillation subsystem 52 to deliver an electrical shock equivalent to the value set at a time equal to time interval 100 after the next pacing spike. Pacing is turned off and the cardiac rhythm is monitored for the presence of ventricular fibrillation.

If ventricular fibrillation was not induced, selector 56 waits a predetermined period of time, preferably about one minute before starting the next test round. Selector 56 is programmed to deliver three rounds of test shocks at the same energy level, at different time intervals in relationship to the pacer spike before lowering the energy level for the test countershock. Therefore, for the next round, timing circuit 58 determines a time interval 104 corresponding to a time point 102 which is preferably 20 msec before the peak 98 of T-wave 94. The heart is shocked at time interval 104 after the next pacer spike. If fibrillation does not occur, the third and last round of testing at this energy level is undertaken with timing circuit 58 determining a time interval 108 corresponding to a time point 106 that is preferably 40 msec before peak 98 and the heart is shocked again. After each shock the cardiac rhythm is monitored to ascertain if the shock has induced ventricular fibrillation.

If after a three shock sequence as described, ventricular fibrillation has not been induced, then selector 56 lowers the shock energy level by a predetermined increment. The new energy level value is stored in memory unit 64. The next round of tests is then initiated beginning with the timing interval 100. The initial energy level chosen for test shocking is variable with a preferable level of 20 J. The amount by which the test shock energy level is reduced is also selectable with a preferred decrement of 5 J. The procedure is repeated until ventricular fibrillation is induced. The last shock strength that does not induce fibrillation is the ULV, which is an accurate estimate of the DFT. If ventricular fibrillation has not been induced after completing all three shocks at the system minimum 5 J level then testing is stopped and the ULV is predicted to be less than or equal to 5 J.

If a test shock induces ventricular fibrillation then the heart is defibrillated with a countershock set at a value incrementally higher than the ULV. Research has determined that a defibrillation countershock 3 J higher than the ULV, and preferably 5 J higher than the ULV, will successfully defibrillate the heart 100% of the time.

Figure 3:
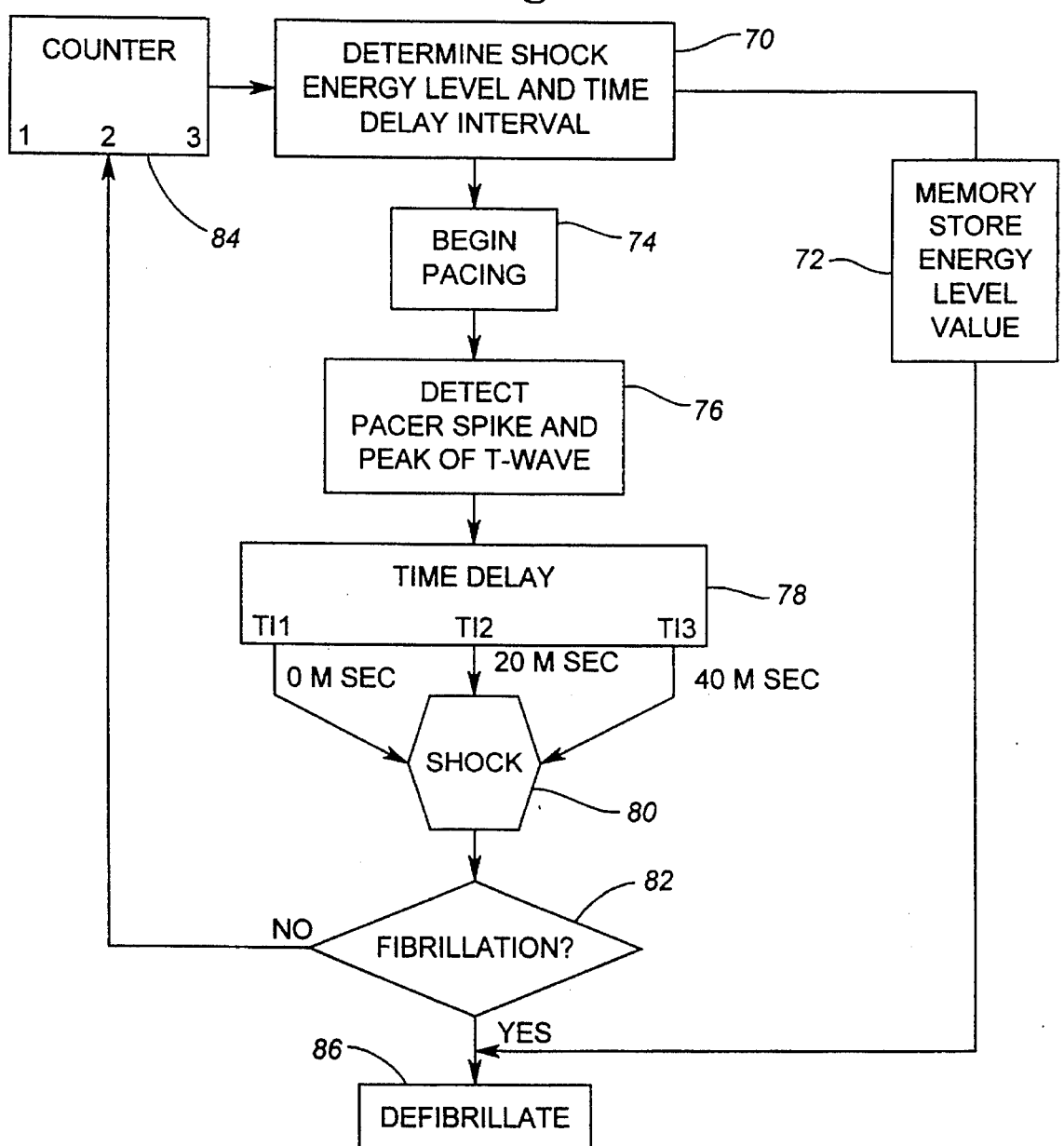
FIG. 3 is a block diagram depicting one possible sequence of steps in accordance with the method of the present invention.

Referring to FIG. 3, the method of the present invention begins with step 70 wherein a shock energy level and a time delay interval are chosen according to a predetermined protocol and in conjunction with any energy level value stored by step 72. The preferred first energy level is 20 J, but may range from 10 J to 30 J. The preferred number of time delay intervals is three. Therefore, for each energy level tested there is a set of three test shocks delivered for that energy level corresponding to each of the three time delay intervals. Step 74 initiates overdrive pacing of the heart. Pacing is confirmed and the ECG morphology analyzed in step 76. Based on the ECG morphology, step 78 calculates a time delay interval based on the time delayed called for in step 70. The present invention calculates the time interval in step 78 as measured from the pacer spike to the peak of the T-wave and chooses, according to the selection from step 70, one of three possible intervals beginning with a first time interval to the peak of the T-wave. The second and third time intervals are preferably a time interval ending 20 msec before the peak of the T-wave and a time interval ending 40 msec before the peak of the T-wave, respectively. Using the first time interval value, beginning with the next available pacer spike, step 80 initiates a test shock to be delivered to the heart at the point in time delayed from the pacer spike. For the first time period, the test shock is delivered at the peak of the T-wave.

Following the delivery of the test shock, the heart is monitored for the induction of ventricular fibrillation at step 82. In most cases, the initial test shock energy is sufficiently high such that fibrillation is not induced. Research indicates that a reasonable initial test shock energy is 20 J. If no fibrillation is detected, the counter is incremented at step 84 and the process is repeated at step 70 selecting the next time delay interval. When an energy level has been tested three times, once each for the three time delay intervals, then step 84 resets the counter to one causing step 70 to incrementally lower the test shock energy level to the next lower energy level from the value stored at step 72. These steps repeat until such time as fibrillation is induced or the testing has been completed through the lowest energy level of 5 J. If fibrillation has not been induced even at the 5 J level, the ULV is calculated to be equivalent to 5 J and the defibrillation energy level is set to a level incrementally above the ULV.

At such time when fibrillation is induced and detected at step 82, the ULV is calculated to be next higher energy level that did not induce fibrillation. This is calculated by incrementally increasing the value stored in memory in step 72 which is the present energy level value that did induce fibrillation. Defibrillation is carried out is step 86 by delivering a countershock having an energy value incrementally above the ULV.

The system and method is devised such that the predetermined initial energy level is sufficiently high such that in the vast majority of cases ventricular fibrillation will not occur with the first set of test shocks. The present invention anticipates that there exist a small number of cases that will fibrillate in response to the first energy level. There are at least two possible alternative steps anticipated by the present invention. The first is to automatically assigning the ULV to be equal to the next highest energy level and that successful defibrillation may be accomplished with a defibrillation energy level incrementally above that.

The second is to adjust up to a next higher energy level and begin the testing process from that higher level. If ventricular fibrillation is not induced at this higher energy level for all three time intervals, then the system can safely determine that the present higher level is the ULV and set a defibrillation energy level incrementally above that. However, for these few cases, this alternative method necessitates exposing the patient to a second episode of ventricular fibrillation induced by the test shocks at the higher level. Research suggests that this potential population is sufficiently small to justify the risk of testing at the higher energy level versus the first method of automatically assuming the ULV is the next higher energy level.

The principal advantage of the present invention is prediction of the transvenous DFT by determining the transvenous ULV with improved accuracy, safety, speed and simplicity. The present invention is substantially improved over previous methods of determining the ULV for purposes of predicting the DFT and is of sufficient accuracy that conventional DFT testing should no longer be necessary. With the present invention, only three shocks are delivered in regular rhythm at each shock strength with an induction of a maximum of one episode of ventricular fibrillation. The time required for the procedure is substantially shortened by diminishing the number episodes of ventricular fibrillation, the number of shocks in regular rhythm and the waiting periods between the shocks. Finally, the present invention is simple to apply because the peak of the T-wave is easily identified.

Research has demonstrated that the ULV determined by the present invention, when used as the DFT to defibrillate a patient's heart, successfully defibrillates 90% of the time with a 95% confidence level of plus or minus 8%. When the DFT is increased to an energy level 3 Joules above the measured ULV, the rate of successful defibrillation is 100% with a confidence level greater than 95%.

The foregoing is considered as illustrative only of the principles of the invention, and since numerous modifications and changes will readily occur to those skilled in the art, it is not desired to limit the invention to the exact construction and operation shown and described, and accordingly, all suitable modifications and equivalents may be resorted to, failing within the scope of the present invention.

We claim:

1. A method for determining an upper limit of vulnerability of a patient's heart for predicting a defibrillation threshold energy for an implantable cardioverter defibrillator device implanted in the patient and electrically connected to a particular arrangement of at least two defibrillation electrodes, at least one of which is intravenously implanted within the heart, and to a pacing electrode and a sensing electrode, said method comprising the device-implemented steps of:

(a) storing criteria in a memory of the device for a first test shock, at least a first, second and third time delay intervals, and a shock decrement value;

(b) setting a shock value at the first test shock;

(c) setting a time delay at the first time delay interval;

(d) delivering a sequence of electrical shocks at the shock value by performing the steps of:

(d1) pacing the heart;

(d2) detecting a peak of a T-wave of electrical activity of the heart;

(d3) using the time delay to determine a shock interval measured from the peak of the T-wave;

(d4) delivering through the defibrillation electrodes an electrical shock to the heart having an electrical energy determined by the shock value and being delivered at a time relative to the peak of the T-wave that corresponds to the shock interval;

(d5) sensing for an induction of ventricular fibrillation; and (d6) if no fibrillation is detected in step (d5), successively repeating step (d) after setting the time delay to the second and then to the third time delay intervals;

(e) if no fibrillation is detected in step (d), decrementing the shock value by the shock decrement value and repeating steps (c)–(d); and (f) if fibrillation is detected in step (d), using the shock value as an upper limit of vulnerability.

2. The method of claim 1 wherein the shock decrement value is a constant value of less than 5.0 Joules.

3. The method of claim 2 wherein the shock decrement value is 3.0 Joules.

4. The method of claim 1 wherein the shock decrement value is a variable value.

5. The method of claim 1 wherein the first, second and third time delay intervals are intervals before the peak of the T-wave.

6. The method of claim 5 wherein the first, second and third time delay intervals are each constants of equal value.

7. The method of claim 6 wherein the first time delay interval is 0 milliseconds, the second time delay interval is 20 milliseconds, and the third time delay interval is 40 milliseconds.

8. The method of claim 1 wherein step (d) further comprises a step (d7) delaying a predetermined period of time between successive sequences of electrical shocks.

9. The method of claim 8 wherein the predetermined period is about one minute.

10. The method of claim 1 wherein step (f) further comprises the step of storing the shock value plus the shock decrement value in the memory of the device as a defibrillation threshold energy value.

11. A system for determining an upper limit of vulnerability of a patient's heart useful for predicting the defibrillation threshold energy of a defibrillation electrode arrangement for an implantable cardioverter defibrillator implanted in the patient including pacing and sensing electrodes intravenously implanted, said system comprising:

a) at least one defibrillation electrode of the defibrillation electrode arrangement adapted to be intravenously implanted within the heart;

b) test shock generator means for providing an electrical test shock through the defibrillation electrode arrangement;

c) pacing means for overdrive pacing the heart;

d) sensing means for sensing the electrical activity of the heart;

e) timing means electrically connected to the pacing means and the sensing means for providing at least three time interval delays timed in relation to the onset of a pacing discharge to the peak of the associated T-wave;

f) test/treatment selector means for incrementally varying the test shock energy level and choosing from among the at least three time interval delays; and g) test shock driver means electrically connected between the timing means, test/treatment selector means and the test shock generator means for driving the test shock generator means to provide a test shock having the test shock level value and time interval delay value selected by the test/treatment selector means wherein test shock generator means delivers an initial test shock to the heart at a predetermined initial energy level at an initial time delayed from the onset of a pacing discharge and continues to deliver subsequent electrical test shocks to the heart by varying the at least three time interval delays and decreasing test shock energy levels under the control of the test/treatment selector means until the heart is induced to fibrillate as sensed by the sensing means such that the test shock energy level of the test shock level immediately prior to the test shock that induced the fibrillation determines the upper limit of vulnerability for said defibrillation electrode arrangement.

12. The system of claim 11 in which the defibrillation threshold energy is a value incrementally higher than the upper limit of vulnerability.

13. The system of claim 12 in which the energy increment is at least 3 Joules.

14. The system of claim 11 in which the timing means provides for at least three time delay intervals comprising time delays measured from the onset of the pacing discharge to a point in time 0 milliseconds before the peak of the T-wave, to a point in time 20 milliseconds before the peak of the T-wave, and to a point in time 40 milliseconds before the peak of the T-wave.

* * * * *